US006897451B2

(12) United States Patent
Kaercher et al.

(10) Patent No.: US 6,897,451 B2
(45) Date of Patent: May 24, 2005

(54) ISOKINETIC GANTRY ARRANGEMENT FOR THE ISOCENTRIC GUIDANCE OF A PARTICLE BEAM AND A METHOD FOR CONSTRUCTING SAME

(75) Inventors: Hans Kaercher, Karben (DE); Stefan Linn, Griesheim (DE); Thomas Zimmerer, Bischofsheim (DE); Dietmar Koch, Gau-Algesheim (DE); Ralf Fuchs, Gross-Zimmern (DE); Walter Bourgeois, Heidelberg (DE); Peter Spiller, Neu-Anspach (DE)

(73) Assignees: MAN Technologie AG, Augsburg (DE); Gesellschaft fuer Schwerionenforschung mit beschraenkter Haftung, Darmstadt (DE)

( * ) Notice: Subject to any disclaimer, the term of this patent is extended or adjusted under 35 U.S.C. 154(b) by 0 days.

(21) Appl. No.: 10/655,616

(22) Filed: Sep. 5, 2003

(65) Prior Publication Data

US 2004/0159795 A1 Aug. 19, 2004

(30) Foreign Application Priority Data

Sep. 5, 2002 (DE) .......................... 102 41 178

(51) Int. Cl.[7] .............................. A61N 5/10; H01J 3/14; F16M 13/00
(52) U.S. Cl. .............................. 250/396 R; 250/492.3; 248/121; 248/122.1; 248/123.11; 248/127; 248/218.4; 248/219.2; 248/575; 248/612; 378/4; 378/5; 378/68; 378/208; 378/210
(58) Field of Search .................... 250/396 R, 492.3; 248/121, 122.1, 123.11, 127, 218.4, 219.2, 575, 612, 637, 638, 672, 674, 676; 378/4, 15, 68, 208, 210, 65, 143, 144, 195–198

(56) References Cited

U.S. PATENT DOCUMENTS 546,013 A * 9/1895 Handly .................. 169/81
3,995,089 A * 11/1976 Hartmann et al. .......... 428/336
5,027,818 A * 7/1991 Bova et al. ................ 600/427
5,117,829 A * 6/1992 Miller et al. ............... 600/427
5,189,687 A * 2/1993 Bova et al. ................. 378/65
5,769,787 A * 6/1998 Lemelson ................. 600/407
5,882,330 A * 3/1999 Lemelson ................. 604/503
5,978,447 A * 11/1999 Carlson et al. ............ 378/132
6,158,708 A   12/2000 Egley et al.
6,219,403 B1 * 4/2001 Nishihara .................. 378/65
6,449,340 B1 * 9/2002 Tybinkowski et al. ...... 378/150
2002/0196893 A1 * 12/2002 Gordon ...................... 378/4
2004/0005027 A1 * 1/2004 Nafstadius .................. 378/65
2004/0120452 A1 * 6/2004 Shapiro et al. .............. 378/19
2004/0159795 A1 * 8/2004 Kaercher et al. ......... 250/396 R
2004/0162457 A1 * 8/2004 Maggiore et al. ........... 600/1

FOREIGN PATENT DOCUMENTS

DE    199 04 675 A1    8/2000
DE    199 07 138 A1    8/2000

* cited by examiner

Primary Examiner—John R. Lee
Assistant Examiner—Bernard E. Souw
(74) Attorney, Agent, or Firm—Rothwell, Figg, Ernst & Manbeck, P.C.

(57) ABSTRACT

The invention relates to an isokinetic gantry arrangement for the isocentric guidance of a particle beam (12), that can be rotated about a horizontal longitudinal axis (16) and has a beam optical system, symbolized by magnets (36, 38, 40), that deflects the particle beam (12) axially infected by a particle beam accelerator, radially and vertically relative to the horizontal longitudinal axis (16), with a largely rotationally-symmetrical primary structure (18) and a secondary structure (30) that holds the magnets (36, 38, 40) and is supported by the primary structure (18), with the secondary structure (30) having a rigidity that is designed so that the vertical displacements of the magnets (36, 38, 40) due to their weight are essentially of equal magnitude (isokinetic) in all the angle of rotation positions of the gantry arrangement (10), and a method for its design.

24 Claims, 5 Drawing Sheets

Figure 1:
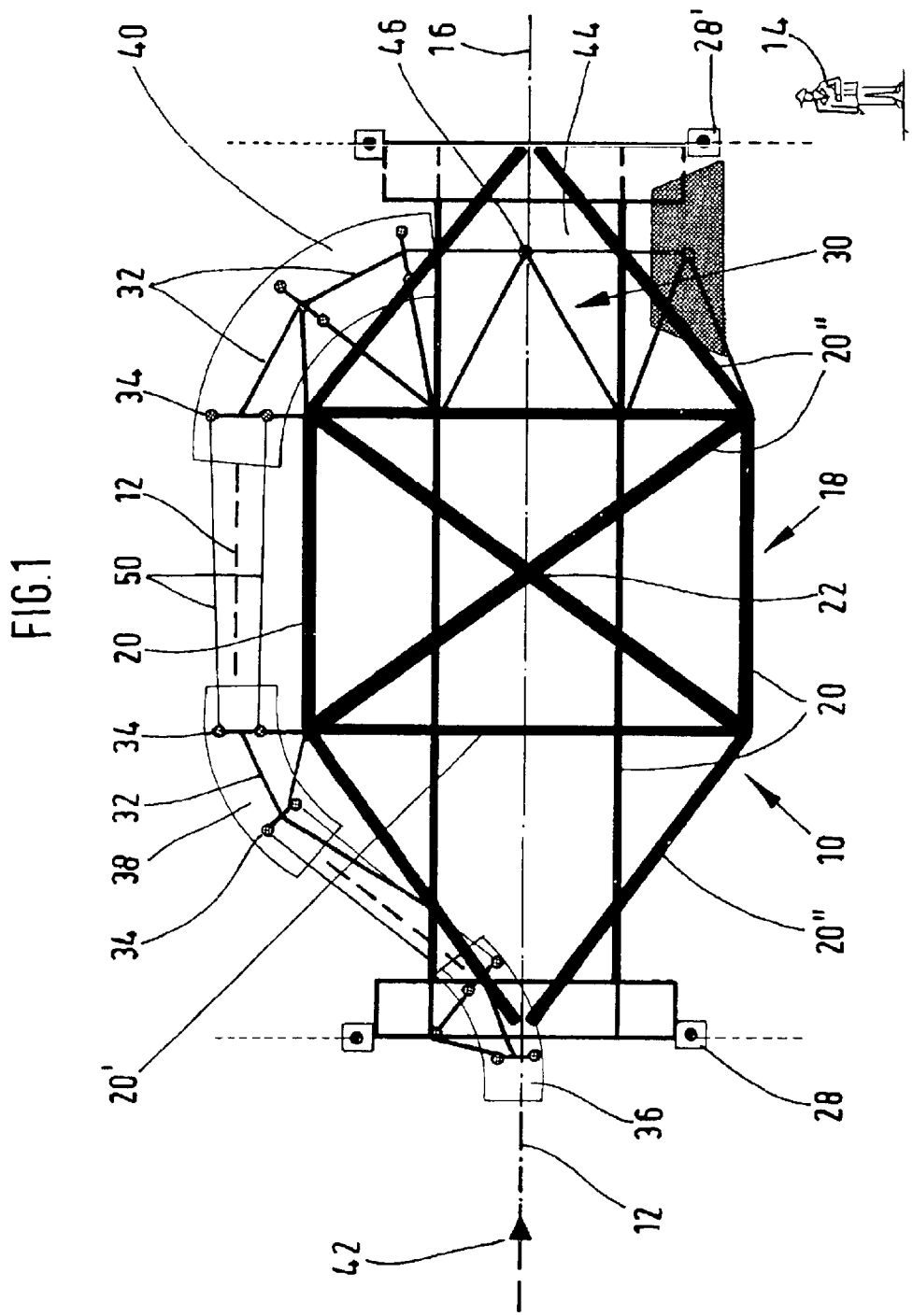

ISOKINETIC GANTRY ARRANGEMENT FOR THE ISOCENTRIC GUIDANCE OF A PARTICLE BEAM AND A METHOD FOR CONSTRUCTING SAME

The invention relates to an isokinetic gantry arrangement for the isocentric guidance of a particle beam and a method for constructing same.

Gantry arrangements, gantry structures or gantries are generally known. Such gantry arrangements are designed for medical technology for the treatment of patients using beams of protons or ions. A distinction is made between gantry arrangements with non-isocentric and gantry arrangements with isocentric guidance of the particle beam.

In the case of the isocentric guidance, the magnets (radiation heads) move in a circle around the patient, i.e. at the same radius, so that the angle of radiation can be freely set. The alignments of the patient on the patient table, that can be moved in three-dimensional directions X-Y-Z and rotated about the vertical axis Z, are comparatively small, particularly in the vertical direction.

In the case of gantry arrangements with non-isocentric guidance of the particle beam, the patient to be treated is aligned relative to the particle beam in a manner that is generally substantially stronger, i.e. brought to the required position in each case or moved from this position to a different position etc. using more physical stress.

With the known proton gantry arrangements with isocentric guidance of the particle beam, the particle beam can be directed to a quite specific (treatment) aim point. The angle of radiation can thus be freely chosen and varied as in conventional (x-ray, gamma ray quanta) radiation therapy. The patient to be treated can himself remain in one and the same position relative to the patient table during the complete treatment. The required travel of the table is very small, and particularly in the vertical Z-direction, regarded as critical, this is only few centimeters, so that access to the patient by the doctor is relative good. These gantry arrangements are used to support and guide heavy magnets on circular routes with relatively large radii, for example, between 2 and 6 meters. This in particular poses the problem that the gantry arrangements, normally designed for rigidity, are subjected to various displacements and/or distortions and/or deformations, depending on the position and (rotational) angle of the magnets. These in turn affect the accurate guidance of the particle beam and are thus detrimental to the accuracy of aim. Added to this is the fact that such gantry arrangements must be extremely rigid, not least because of the stringent requirements with regard to accuracy of aim of the particle beam guidance, and therefore are mostly large extremely heavy structures.

The problem of the high dead weight of the structure is even greater with rigidly-dimensioned gantry arrangements used for radiation treatment with (heavy) ions compared with rigidly-designed gantry arrangements used for therapy using protons (light ions), because their magnets and the beam guidance elements arranged between the magnets are sometimes heavier by a factor of 10 or more. Such extraordinarily large dead weight of the structure in turn leads to displacements and/or distortions and/or deformations within the gantry arrangements that in turn detrimentally effect the required accuracy of aim, because, as structural analysis has shown, the amount of deformation resulting from the dead-weight of heavy-ion gantries is greater.

The object of this invention is therefore to provide an isokinetic gantry arrangement for the isocentric guidance of a particle beam, by means of which the above disadvantages can be prevented, and which is thus of particularly simple design, enables a distinctly high accuracy of aim of the particle beam in all angle of rotation positions of the gantry arrangement without the necessity of a (moreover constant) field strength readjustment of the magnets or beam guidance elements, and also has a relatively low weight, as well as providing a method for the design of such a gantry arrangement.

The object is achieved in a surprisingly simple manner with regard to the technical structure by means of the features of claim 1.

By means of the embodiment in accordance with the invention of the gantry arrangement for isocentric guidance of a particle beam in accordance with the features of claim 1, a particularly simple isokinetic gantry arrangement can be achieved. This is on one hand rotatable about a horizontal longitudinal axis and has magnets the overall effect of which is to result in the guidance of a particle beam axially injected by a particle accelerator, radially and vertically relative to the horizontal longitudinal axis. Furthermore, this has a largely rotationally-symmetrical primary structure and a less rigid magnet-mounting secondary structure supported by the primary structure with the secondary structure having a rigidity designed such that the vertical displacements of the magnets due to the their weight in all angle of rotation positions of the gantry arrangement are essentially of equal magnitude (isokinetic). Therefore proceeding from this, an extremely high accuracy of the particle beam is enabled in all angle of rotation positions of the gantry arrangement, so that with regard to this practically no additional expense is required to compensate for inaccuracies. These include, for example, lever systems for weight equalization or an additional constant field strength readjustment of the magnets or of the beam guidance elements. Because less rigid structural components are integrated (secondary structure) and therefore from the start enable better displacements and/or distortions and/or deformations than will otherwise be the case, the isokinetic gantry arrangement in accordance with the invention also has the essential advantage of on one hand being substantially lighter due to the improved use of materials and on the other hand having a relatively small structural height, i.e. reduced dimensions. Both in turn promote the accuracy of aim of the particle beam. At the same time, the less rigid design of the structural areas contributes to substantial savings in materials. With the gantry arrangement in accordance with the invention, the preconditions for a very good isocentric guidance of the particle beam are therefore realized, without the structure turning out to be too solid and costly. The gantry structure in accordance with the invention is finally as equally suitable for the guidance of proton beams (light ions) as of (heavy) ions.

Advantageous structural details of the gantry arrangement in accordance with the invention are described in claims 2 to 22.

In a particularly advantageous manner, it is provided in accordance with the features of claim 2 that the secondary structure has a rigidity that is designed in such a way that vertical displacements of the magnets due to their weight are of equal magnitude in all angle of rotation positions of the gantry arrangement.

Of particular significance are the features of claim 3, in accordance with which the magnets can be moved on circular tracks around an axis of rotation that is displaced relative to the horizontal longitudinal axis of the gantry arrangement in the unloaded state. For this purpose, the magnets in accordance with the invention are guided on circular tracks that run in planes that are vertical or slightly inclined relative to the horizontal longitudinal axis or rotational axis. The circular tracks are set during a computer-aided design phase with the aid of a structure-deformation analysis by using appropriate fine dimensioning of the structural components, particularly with regard to the choice of their cross-sections.

An advantageous embodiment of the gantry arrangement in accordance with the invention is in the common specification of the radiation aim point and the displacement of the rotational axis due to loads, which moves somewhat in space due to the angular position of the gantry. In accordance with claim 4, this lies in the fact that the "intersection point" between the ion/proton beam and the load displaced theoretical rotational axis, that can be determined relative to the horizontal longitudinal axis of the gantry arrangement in the unloaded state by means of the method of in the smallest error squares from load displacements, is used as the radiation aim point.

Furthermore, as part of the invention, the primary structure corresponding to claims 5 to 8 can be formed as a three-dimensional framework consisting essentially of horizontal and vertical beams and of diagonals that form beams, that in part intersect each other in the centre of the area at the ends of which two, particularly box-shaped member support rings are provided that interact with fixed bearing pedestals. In this case it is useful if one of the two fixed bearing pedestals is designed as a floating bearing and the other of the two fixed bearing pedestals as a fixed bearing.

Of particular design significance for reducing the weight and mass forces on one hand and increasing the accuracy of aim of the particle beam on the other hand are the measures of claim 9, whereby the magnet-mounting secondary structure supported by the primary structure is of less rigid construction than the primary structure.

In a completely advantageous embodiment of the gantry arrangement in accordance with the invention, the magnet-mounting secondary structure supported by the primary structure in accordance with claim 10 is connected to the primary structure in a manner that adds additional torsional rigidity to the tilting movements of the magnets in azimuth, which enables the accuracy of aim of the particle beam to be further improved.

Furthermore, it is possible as part of the invention to advantageously equip the gantry arrangement with a secondary structure supported by the primary structure that in accordance with claims 11 to 18 contains at least one, particularly three, magnets with several beam guidance elements, such as steerer and quadrupoles, are located between the magnets, but which are not dealt with further here because these, in contrast to the magnets, have less influence on the deformation behavior of the gantry structure.

In this context, it has shown itself to be advantageous to arrange the first magnet, in accordance with the measures of claim 14, on the horizontal longitudinal axis cantilevered on the primary structure by means of long members and provide a connection by means of struts for the second and third magnets, thus enabling the "large" movements of the central gantry area to be accompanied, largely isokinetic, by the magnets.

An advantageous embodiment of the gantry arrangement in accordance with the invention is obtained in accordance with claim 19 by using magnets that are designed to take and guide a particle beam of protons. Accordingly, the gantry arrangement in accordance with the invention can be advantageously used as a so-called proton gantry.

As an alternative, it is of particularly great significance in accordance with the invention that the magnets are designed in accordance with the features of claim 20 to take and guide a particle beam of ions. Thus, the gantry arrangement in accordance with the invention can be advantageously used as a so-called ion gantry. Because the magnets and particle flow guidance elements required for the beam guidance of an ion gantry are substantially larger and heavier than for a proton gantry, the improvements achievable by the invention are mainly in the size and dimensional conditions of the gantry arrangement overall and the expenditure on materials and thus lead to a substantial cost saving.

In accordance with claim 21, particle beam guidance elements are arranged between the magnets.

Appropriately, the second and third magnets form an integral unit corresponding to the measures of claim 22.

The object is also achieved with regard to the technical process in a surprisingly simple manner by the features of claim 23.

Accordingly, by means of a method in accordance with the invention to design a gantry arrangement with isocentric guidance of a particle beam, the rigidity of an essentially rotationally-symmetrical primary structure is designed in such a way that the vertical displacements of the magnets due to their weight in all angle of rotation positions of the gantry arrangement are largely of equal magnitude, preferably of equal magnitude, with the magnets moving on circular tracks around an axis of rotation that in the unloaded state is displaced relative to the horizontal longitudinal axis of the gantry arrangement. In this way, a gantry arrangement can be obtained that is of simple design but at the same time enables an extremely high accuracy of aim of the particle beam in all angle of rotation positions of the gantry arrangement. An essential aspect of the method in accordance with the invention is that displacements and/or distortions and/or deformations are achievable in the design and dimensioning that are far greater and thus can be better influenced from the outset than would otherwise be possible, that lead to a gantry arrangement that is substantially lighter and smaller in construction due to the improved used of materials and can therefore be very cost-effectively manufactured.

Finally, in this context it is still possible as part of the invention to determine the theoretical axis of rotation, reduced due to load, in accordance with claim 24 relative to the horizontal longitudinal axis of the gantry arrangement in the unloaded state by using the method of the smallest error squares and to define the "intersection point" between the ion/proton beam and the load-displaced theoretical rotational axis as the radiation aim point.

Further features, advantages and details of the invention are given in the preferred embodiments of the invention described in the following, with the aid of drawings, These drawings are as follows:

FIG. 1 A schematic side view of an embodiment of a gantry arrangement designed in accordance with the invention.

Figure 2:
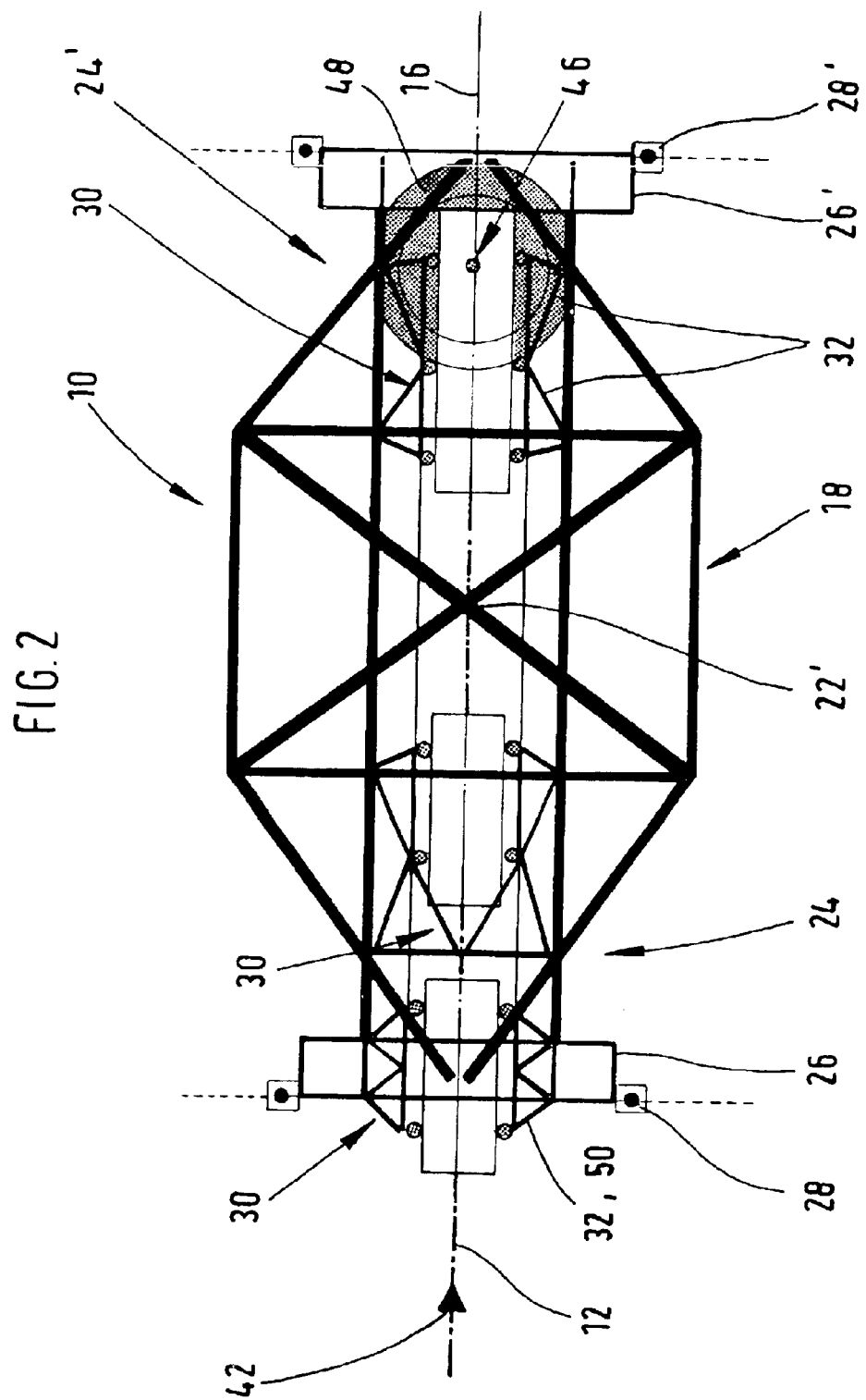

FIG. 2 A schematic plan view of an embodiment of a gantry arrangement in accordance with FIG. 1 designed in accordance with the invention.

Figure 3:
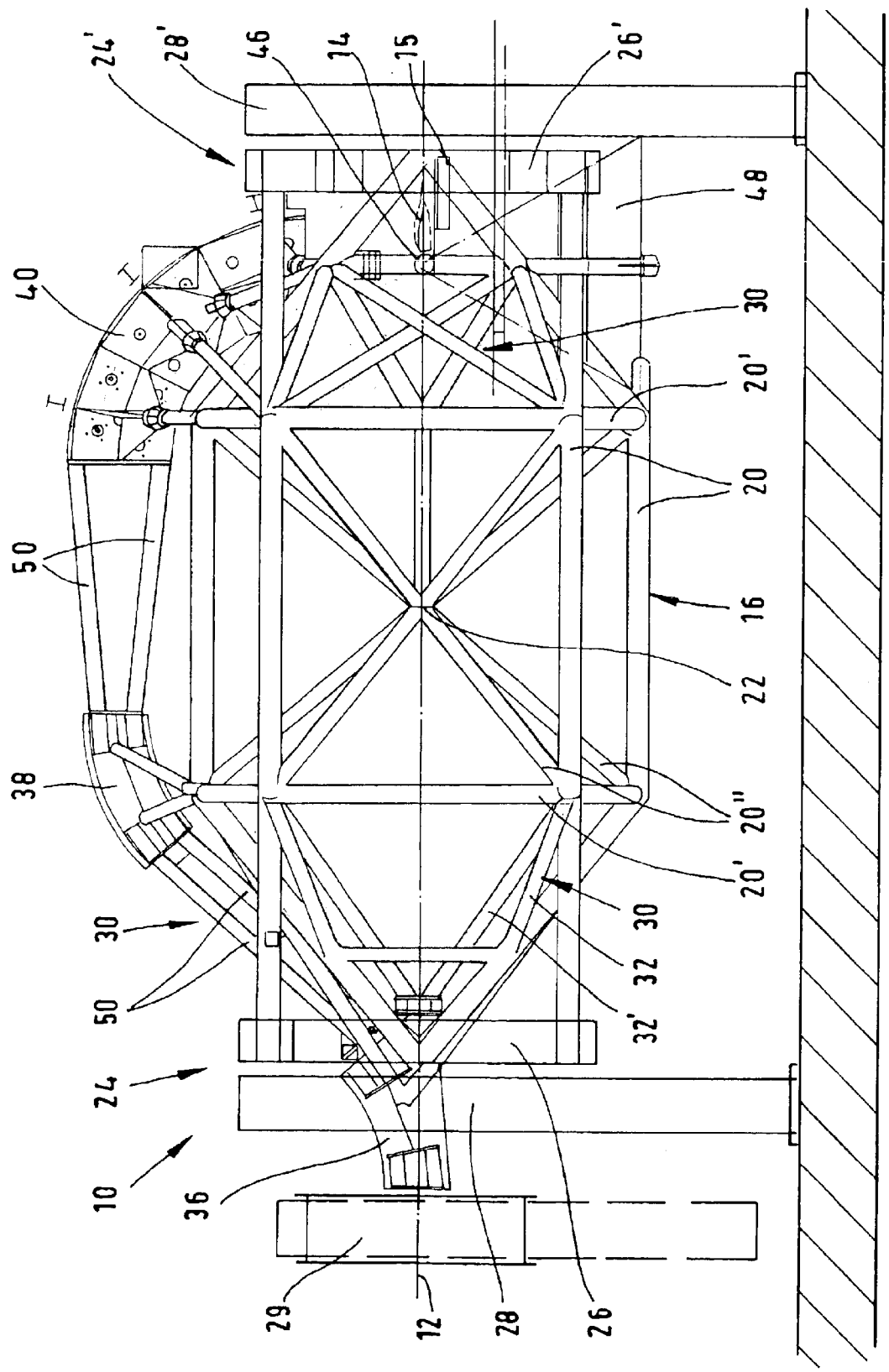

FIG. 3 A side view of a different embodiment of a gantry arrangement designed in accordance with the invention, as an enlarged view.

Figure 4:
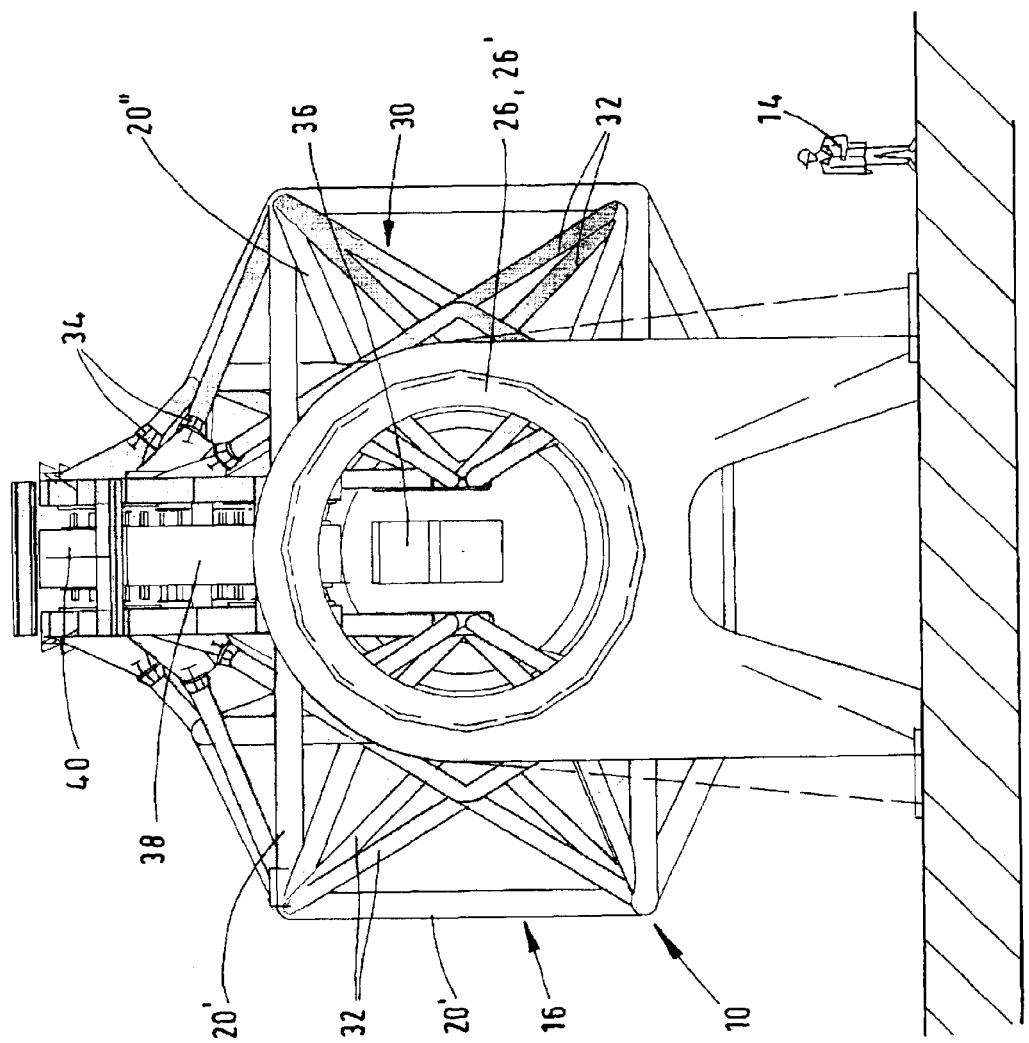

FIG. 4 A front view of an embodiment of the gantry arrangement designed in accordance with the invention, as shown in FIG. 3.

Figure 5A:
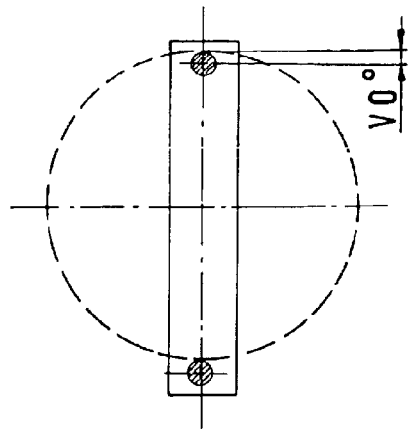
Figure 5B:
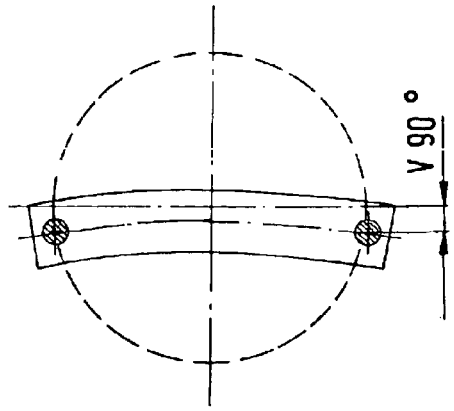

FIGS. 5A and 5B Schematic cross-sectional view of an embodiment of the gantry arrangement designed in accordance with the invention, as shown in FIGS. 3 and 4, showing two different angle of rotation positions or settings of the gantry arrangement.

Figure 6:
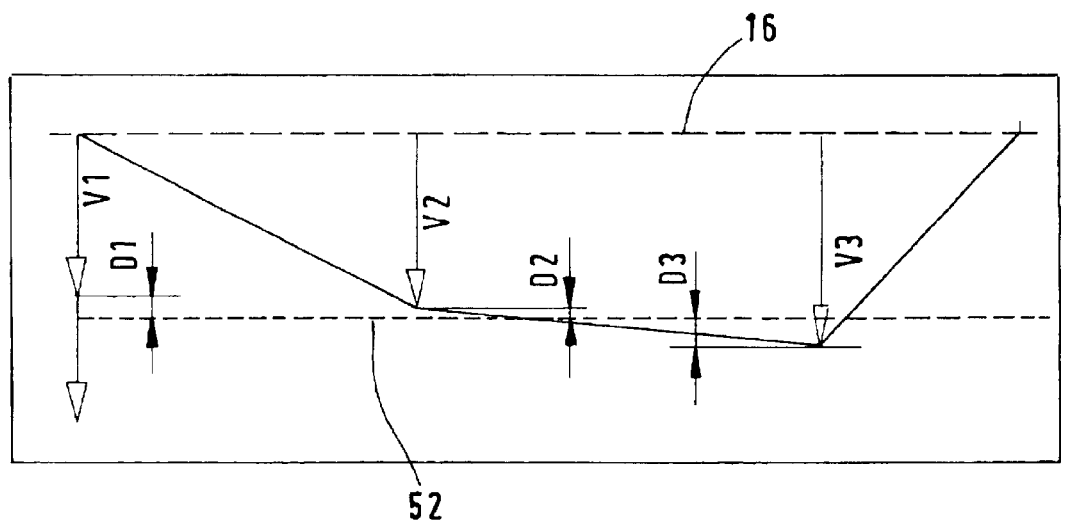

FIG. 6 A schematic bar chart of an embodiment of the gantry arrangement designed in accordance with the invention, as shown in FIGS. 3 and 4, to illustrate the displacements and/or distortions and/or deformations that are caused by the weight of the magnets and/or particle beam guidance elements.

In the following description of an embodiment of a gantry arrangement in accordance with the invention 10 for isocentric guidance of a particle beam 12, parts that correspond to each other are given identical reference characters in each case.

The embodiment shown is a gantry arrangement provided for the guidance of proton beams, particularly heavy ions. Thus, the radiation of patients with ions, for example carbon, is shown to be a promising treatment that enables deep tumors to be accurately located and killed, with the adjacent sound tissue outside the tumor volume remaining largely untouched. Heavy ion rays are in this case biologically substantially more efficiency than proton rays.

FIGS. 1, 2 and/or 3, 4 show the general construction of an embodiment of such a gantry arrangement 10 in accordance with the invention, for isocentric guidance of a particle beam, i.e. ion ray 12. The dimensions and size relationships of a gantry arrangement 10 of this kind are shown relative to the size of a human 14.

The gantry arrangement 10 can rotate about a horizontal longitudinal axis 16 and has a primary structure 18 that is largely rotationally symmetrical. The primary structure 18 is constructed as a three-dimensional framework consisting essentially of horizontal members 20, vertical members 20' and diagonal members 20". The diagonal members 20", for example, stiffen the rectangular framework of the primary structure 18 and intersect in the central points 22, 22' of the area.

Furthermore, the primary structure 18 has at its ends 24, 24' two member support rings 26, 26' in the form of box members or similar, that interact with fixed bearing pedestals 28, 28'. The rotational joint between the primary structure 18 and the fixed bearing pedestals 28, 28' is produced by box-shaped member support rings 26, 26'. One bearing pedestal 28 of the two stationary bearing pedestals 28, 28' is in this case designed as a floating bearing. The other bearing pedestal 28' of the two stationary pedestal bearings 28, 28' is designed as a fixed bearing.

The secondary structure 30 carried by the primary structure 18 is optimized with regard to weight and rigidity so that vertical flexing and/or displacements and/or distortions and/or deformations due to magnets 36, 38 and 40 are of approximately equal magnitude in all angle of rotation positions or angle of rotation settings of the gantry arrangement 10. In a preferred manner, the secondary structure 30 is stiffened so that these vertical displacements are of equal magnitude in all the angle of rotation positions of the gantry arrangement 10.

The primary structure 18 carries a cable turning or trailing device 29, shown only schematically in FIG. 3.

The primary structure 18 supports the secondary structure 30. The secondary structure 30 is constructed of members 32 and coupling elements 34 to take and/or retain and attach magnets 36, 38, 40 as well as particle beam guidance elements (not illustrated) arranged between the magnets 36, 38, 40 and struts 50.

With the examples of embodiments of the gantry arrangement 10 shown in FIGS. 1 to 4, three magnets 36, 38, 40 are fitted in each case to guide the particle beam 12. Magnets 36, 38, 40 guide the particle beam 12, that is axially injected by a particle accelerator, in this case by a proton or ion accelerator (not illustrated), as shown by arrow 42, so that it is guided radially, i.e. vertical to the horizontal longitudinal axis 16, to a patient space 44 and strikes the planned (treatment) point of aim 46. The patient 14 can thus be treated in the horizontal position precisely at the (treatment) point of aim 46. By means of the patient table 15, the patient and thus the tumor can be positioned precisely relative to the point of aim 46 in three-dimensional directions (X-Y-Z) and rotated about the vertical axis Z to achieve the necessary angular position. The particle beam 12 terminating in the patient space 44 is captured by a screening block 48 that can also serve as a counterweight for the complete gantry arrangement 10.

In particular, a first magnet 36 is arranged facing towards a particle accelerator on the horizontal longitudinal axis 16. The first magnet 36 is used to take the particle beam 12 that is axially injected and deflect it from the horizontal longitudinal axis 16. Relative to the radial plane of the beam, the first magnet 36 rotates the axially injected particle beam 12 about a preset angle of approximately 30° to 60°, particularly about approximately 45°, from the longitudinal axis 16. For this purpose, the first magnet 36 is freely or floating mounted on the longitudinal axis 16 on the primary structure 18 by means of struts 50', in particular it is mounted quasi-cantilevered and axially-symmetrical.

The second magnet 38 is designed to take the particle beam 12 coming from the first magnet 36 and turn back the beam on a path parallel to the horizontal longitudinal axis 16. It therefore rotates the particle beam back by a preset angle of approximately 30° to 60°, particularly about approximately 45°, until it again runs parallel to the horizontal longitudinal axis.

The third magnet 40 is used to take the particle beam 12 coming from the second magnet 38, to deflect the beam in the patient space 44, radially and vertically relative to the horizontal longitudinal axis 16, to the precise (treatment) point of aim 46. The third magnet 40 deflects the particle beam 12 radially and essentially vertical relative to the horizontal longitudinal axis 16 by an angle of between approximately 60° to 120°, particularly by about 90°.

In principle fewer or more magnets than shown here can be used to deflect the particle beam. In particular, magnets 38 and 40 can be combined to form a unit that deflects the particle beam by approximately 120° to 150°.

The secondary structure 30, holding magnets 36, 38, 40, supported by the primary structure 18 is mounted on the primary structure 18 in such a way that it has torsional rigidity with regard to tilting movements of magnets 36, 38, 40 in azimuth.

Magnets 36, 38, 40 themselves move on the circular track about an (imaginary) axis of rotation 52 that in the unloaded state is displaced relative to the horizontal longitudinal axis 16 of the gantry arrangement 10. As the size comparison with a human 14 shows, the second and third magnets 38, 40 are guided on considerable radii. The axis of rotation 52 in this case is preferably determined relative to the horizontal longitudinal axis 16 of the gantry arrangement 10 by using the vertical resilient displacements of the magnets by means of the method of the smallest error squares.

The secondary structure 30, that is supported by the primary structure 18 and takes and holds the magnets 36, 38, 40, is furthermore of a resilient or flexible design compared to that of the primary structure 18.

Because of the great weight of the magnets 36, 38, 40 including the particle beam guidance elements and the ever-present elasticity of beam structures generally, a sag of the gantry arrangement 10 occurs, the extent of which varies according to the angle of rotation position. There is also the added factor that the deformation differs depending on the different angle of rotation positions of the gantry arrangement 10.

FIGS. 5A and 5B illustrate these deformations for the magnets and counterweight 48 for two different positions of the gantry. In order to be able to realize vertical displacements V2, V3 of magnets 38, 40 that are as equal as possible in any angle of rotation positions of the gantry arrangement 10, it is necessary to use their maximum displacements as a datum. Because of the considerable lever effects on the gantry arrangement 10, these result at the horizontal positions of −90° and +90° of the magnets 38, 40. Taking account of these maximum displacements, the secondary structure 30 is designed to be correspondingly soft in the vertical direction and rigid in azimuth, in order to preclude unwanted tilting movements of the magnets 36, 38, 40.

The gantry arrangement 10 in accordance with the invention ensures that the particle beam 12 constantly strikes one and the same (treatment) point of aim 46 without corrective intervention to the fields of the magnets or to the particle beam guidance elements, regardless of the angle of rotation position of the magnets 36, 38, 40.

So that the particle beam 12 strikes the (treatment) point of aim 46 with the highest possible precision in all angle of rotation positions of the magnets 36, 38, 40, the gantry arrangement 10, despite resilient deformation displacements, guides the magnets 36, 38, 40 about the common horizontal axis of rotation 52 on circular tracks, designed in such a way that their positions relative to each other do not shift. The original horizontal particle beam is deflected by exactly 90°. The particle beam 12 thus lies in the circular plane of the third magnet 40 and strikes the (treatment) point of aim 46 always in the mid point of the circle of all the angle of rotation positions.

The constructive design of the gantry arrangement 10 according to the invention is therefore based on the following:

It was initially intended to design a gantry arrangement according to the generally-known basic principles of prior art that would be as rigid as possible. Simulation calculations however, showed that the vertical displacements V1, V2, V3 of the three magnets 36, 38, 40 could not be reduced as required because of the increasing deadweight of the gantry arrangement 10 overall.

To achieve the necessary accuracy and at the same time reduce the deadweight and thus the costs, the isokinetic gantry was developed. It contains an ideal structure that under the load of the magnets 36, 38, 40, including its deadweight, has the same deformation displacements (V1=V2=V3=VH) in all three angle of rotation positions. The magnets 36, 38, 40 thus move on circular tracks about the axis 52, that is displaced by the amount of VH relative to the longitudinal axis 16 of the unloaded bearings 28, 28'.

Furthermore, with the gantry arrangement 10 in accordance with the invention, when the particle beam 12 is aligned it strikes in one and the same (treatment) point of aim 46, in all three angle of rotation positions, provided the connection of the magnets 36, 38, 40 to the gantry structure 10 is quasi-rigid in the azimuth direction with regard to tilting movements. This (treatment) point of aim 46 is the intersection point between the axis of rotation 52 and the particle beam 12 radially deflected by 90°. The gantry arrangement 10 has no deformation displacements relative to this intersection point.

Because in relation to the horizontal axis 52 only the relative displacements of the particle beam guidance elements relative to each other are determinant and not the absolute displacements, absolute displacements of greater amounts are readily permissible. This results in considerable savings in materials because certain structural areas can be of relatively thin-walled design. Compared with a gantry that is designed for rigidity, the gantry arrangement 10 in accordance with the invention requires significantly less steel.

FIG. 6 shows an example of the realized displacements V1, V2, V3 of the three magnets 36, 38, 40 including the axis of rotation 52. Because displacement V1 of the softly-mounted first magnet 36 is practically the same in all angle of rotation positions of the gantry arrangement 10 with symmetrical restraint and can be easily determined by the design, the selection of the displacement V1 for the horizontal axis of rotation 52 is further optimized so that it is approximately the same (V2+V3)/2.

Because magnets 36, 38, 40 move in a circular motion when viewed in the direction of the axis and not in an approximately elliptical track, the displacements V2 and V3 should also be chosen to be as equal as possible, which can be realized as part of a fine optimization for several angle of rotation positions.

In accordance with FIG. 6, the position of the horizontal axis of rotation 52 is, for example, selected according to the principle of the smallest error squares with regard to distances D1, D2 and D3. In this way it lies between V1, V2 and V3.

The invention is not limited to the forms of embodiment shown. It is therefore readily possible to use the isokinetic gantry arrangement 10 in accordance with the invention equally for treatment using proton rays. In this case the structural design of such a gantry arrangement is essentially identical. All that changes is the size relationships due to the different weights and dimensions of the magnets and particle beam guidance elements. Without being shown in detail, it is also conceivable to support not only three magnets 36, 38, 40 but instead fewer or more than three magnets by means of the gantry arrangement 10 in accordance with the invention. It is thus, for example, possible to combine the second and third magnets structurally to form a single unit.

What is claimed is:

1. Gantry arrangement for the isocentric guidance of a particle beam (12) that can be rotated about a horizontal longitudinal axis (16) and has a beam optical system symbolized by magnets (36, 38, 40) that radially and vertically relative to the horizontal longitudinal axis (16) deflect a particle beam (12) that has been axially injected by a particle beam accelerator, with an extensive rotationally-symmetrical primary structure (18) and a secondary structure (30) supported by the primary structure (18) and holding the magnets (36, 38, 40), with the secondary structure (30) having a rigidity that is designed such that vertical displacements of the magnets (36, 38, 40) due to their weight are essentially of the same magnitude (isokinetic) in all the angle of rotation positions of the gantry arrangement (10).

2. Gantry arrangement in accordance with claim 1, characterized in that, the secondary structure (30) has a rigidity that is designed such that vertical displacements of the magnets (36, 38, 40) due to their weight are of equal magnitude in all angle of rotation positions of the gantry arrangement (10).

3. Gantry arrangement in accordance with claim 1, characterized in that, the magnets (36, 38, 40) can move on circular tracks about an axis of rotation (52) that is displaced in the unloaded state relative to the horizontal longitudinal axis (16) of the gantry arrangement (10).

4. Gantry arrangement in accordance with claim 3, characterized in that, as a radiation point of aim, the intersection point between the particle beam and the load-displaced axis of rotation (52) is used, that with respect to the horizontal longitudinal axis (16) of the gantry arrangement (10) in the unloaded state can be determined from the load displacements of the magnets (36, 38, 40) using the method of the smallest error squares.

5. Gantry arrangement in accordance with claim 1, characterized in that, the primary structure (18) is designed as a three-dimensional framework consisting essentially of horizontal and vertical members (20, 20') and diagonal members (20").

6. Gantry arrangement in accordance with claim 5, characterized in that, some of the diagonal members (20") stiffen the rectangular frame of the primary structure (18) and intersect in the centre points (22, 22') of the surface.

7. Gantry arrangement in accordance with claim 1, characterized in that, the primary structure (18) has at its ends (24, 24') two, particularly box-shaped, member support rings (26, 26') that interact with fixed bearing pedestals (28, 28').

8. Gantry arrangement in accordance with claim 7, characterized in that, one (28) of the two fixed bearing pedestals (28, 28') is designed as a floating bearing and the other (28') of the two fixed bearing pedestals (28, 28') is designed as a fixed bearing.

9. Gantry arrangement in accordance with claim 1, characterized in that, the secondary structure (30) holding the magnets (36, 38, 40) and supported by the primary structure (18) is of a less-rigid design than the primary structure (18).

10. Gantry arrangement in accordance with claim 1, characterized in that, the secondary structure (30) holding the magnets (36, 38, 40) and supported by the primary structure (18) is attached to the primary structure (18) so as to be torsionally stiff with respect to tilting movements of the magnets (36, 38, 40) in azimuth.

11. Gantry arrangement in accordance with claim 1, characterized in that, the secondary structure (30) supported by the primary structure (18) has at least one, in particular three, magnet(s) (36, 38, 40).

12. Gantry arrangement in accordance with claim 11, characterized in that, a first magnet (36) is essentially arranged on the horizontal longitudinal axis (16) facing towards the particle accelerator, to take the axially injected particle beam (12) and to deflect it from the horizontal longitudinal axis (16).

13. Gantry arrangement in accordance with claim 12, characterized in that, the first magnet (36) deflects the axially injected particle beam (12) from the horizontal longitudinal axis (16) by an angle approximately between 30° to 60°, in particular of approximately 45°.

14. Gantry arrangement in accordance with claim 12, characterized in that, the first magnet (36) is cantilever mounted on the primary structure (18) on the horizontal longitudinal axis (16) above long members (32').

15. Gantry arrangement in accordance with claim 11, characterized in that, a second magnet (38) is provided to take the particle beam (12) coming from the first magnet (36), and deflect it parallel to the horizontal longitudinal axis (16), and is coupled to the first magnet by struts (50).

16. Gantry arrangement in accordance with claim 15, characterized in that, the second magnet (38) deflects the particle beam (13), deflected by the first magnet (36), back parallel to the horizontal longitudinal axis (16) by an angle of approximately between 30° to 60°, in particular by approximately 45°.

17. Gantry arrangement in accordance with claim 11, characterized in that, a third magnet (40) is provided to take the particle beam (12) coming from the second magnet (38), that deflects it radially and vertically relative to the horizontal longitudinal axis (16) and is coupled to the second magnet by struts (50).

18. Gantry arrangement in accordance with claim 17, characterized in that, the third magnet (40) deflects the particle beam (12) coming from the second magnet (38), radially and essential vertical to the horizontal longitudinal axis (16) by an angle of approximately between 60° to 120°, in particular by approximately 90°.

19. Gantry arrangement in accordance with claim 1, characterized in that, the magnets (36, 38, 40) are designed to take and deflect a particle beam (12) of protons.

20. Gantry arrangement in accordance with claim 1, characterized in that, the magnets (36, 38, 40) are designed to take and deflect a particle beam (12) of ions.

21. Gantry arrangement in accordance with claim 1, characterized in that, particle beam guidance elements are arranged between the magnets (36, 38, 40).

22. Gantry arrangement in accordance with claim 1, characterized in that, the second and third magnets form an integrated unit.

23. Method for design of a gantry arrangement (10) for the isocentric guidance of a particle beam (12) in accordance with one of the preceding claims, by means of which the rigidity of a primary structure (18) that is essentially rotationally-symmetrical is designed in such a way that the vertical displacements of the magnets (36, 38, 40) due to their weight are essentially of equal magnitude, preferably of exactly equal magnitude, in all the angle of rotation positions of the gantry arrangement (10), with the magnets (36, 38, 40) moving on circular tracks about an axis of rotation (52) that is displaced with respect to the horizontal longitudinal axis (16) of the gantry arrangement (10) in the unloaded state.

24. Method in accordance with claim 23, characterized in that, the theoretical axis of rotation (52) lowered due to loads is determined with respect to the horizontal longitudinal axis (16) of the gantry arrangement (10) in the unloaded state by means of the method of smallest error squares and the "intersection point" between the particle beam and the load-displaced theoretical axis of rotation (52) is defined as the radiation point of aim.

* * * * *